(12) United States Patent
Jewell et al.

(10) Patent No.: US 10,392,337 B2
(45) Date of Patent: Aug. 27, 2019

(54) PROCESS FOR PURIFICATION OF METHYL METHACRYLATE

(71) Applicant: Dow Global Technologies LLC, Midland, MI (US)

(72) Inventors: Dennis W. Jewell, Angleton, TX (US); John G. Pendergast, Jr., Pearland, TX (US); William G. Worley, Missouri City, TX (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 15/768,027

(22) PCT Filed: Sep. 28, 2016

(86) PCT No.: PCT/US2016/054043
§ 371 (c)(1),
(2) Date: Apr. 13, 2018

(87) PCT Pub. No.: WO2017/065969
PCT Pub. Date: Apr. 20, 2017

(65) Prior Publication Data
US 2018/0297930 A1    Oct. 18, 2018

Related U.S. Application Data

(60) Provisional application No. 62/241,345, filed on Oct. 14, 2015.

(51) Int. Cl.
*B01D 3/06* (2006.01)
*B01D 3/14* (2006.01)
(Continued)

(52) U.S. Cl.
CPC .............. *C07C 67/54* (2013.01); *B01D 3/141* (2013.01); *B01L 3/06* (2013.01); *B01L 3/14* (2013.01);
(Continued)

(58) Field of Classification Search
CPC ....... C07C 51/44; C07C 51/445; C07C 57/04; C07C 69/54; C07C 67/54; B01D 3/06; B01D 3/14
See application file for complete search history.

(56) References Cited

U.S. PATENT DOCUMENTS 4,733,005 A    3/1988    Schmidt et al.
7,118,653 B2  10/2006    Brady et al.
(Continued)

FOREIGN PATENT DOCUMENTS

JP    2005239564 A    9/2005

OTHER PUBLICATIONS

US 8,858,761 B2, 10/2014, Kyu et al. (withdrawn)
(Continued)

*Primary Examiner* — Jafar F Parsa
(74) *Attorney, Agent, or Firm* — Brian L. Mutschler

(57) ABSTRACT

A process for purifying methyl methacrylate. The method comprises: (a) feeding a product mixture comprising methyl methacrylate, methanol, water and oligomers of methyl methacrylate to a divided section of a distillation column comprising a dividing wall; (b) removing an overhead stream and a bottoms stream from the distillation column, and removing a middle side draw stream from the distillation column; wherein the crude product enters the dividing wall distillation column in a divided section on an opposing side of the dividing wall from the middle side draw stream; and (c) removing an upper side draw stream from a point above the dividing wall and below the top of the distillation
(Continued)

column, separating a portion of water from the upper side draw stream to produce a dewatered upper side draw stream and returning the dewatered upper side draw stream to the distillation column.

10 Claims, 1 Drawing Sheet

(51) Int. Cl.
    *C07C 51/44*     (2006.01)
    *C07C 57/04*     (2006.01)
    *C07C 67/54*     (2006.01)
    *C07C 69/54*     (2006.01)
    *B01L 3/14*     (2006.01)
    *B01L 3/06*     (2006.01)

(52) U.S. Cl.
    CPC ............ *C07C 51/44* (2013.01); *C07C 51/445* (2013.01); *C07C 57/04* (2013.01); *C07C 69/54* (2013.01)

(56) References Cited

U.S. PATENT DOCUMENTS

| | | |
|---|---|---|
| 7,956,157 B2 | 6/2011 | Butler |
| 8,410,323 B2 | 4/2013 | Sawant et al. |
| 8,932,434 B2 | 1/2015 | Lee et al. |
| 9,481,629 B2 | 11/2016 | Merenov et al. |
| 2010/0112362 A1 | 5/2010 | Craciun et al. |

OTHER PUBLICATIONS

Endo et al., method for producing (Meth)acrylic acid ester, JP 2005239564 (machine translation), Sep. 2005.*

Le, et al., "Dividing wall columns for heterogeneous azeotropic distillation", Chem. Eng. Research and Design, vol. 99, pp. 111-119 (2015).

Barroso-Munox, et al., "Implementation and Operation of a Dividing-Wall Distillation Column", Chem. Eng. Technol., vol. 34, No. 5, pp. 746-750 (2011).

Sandoval-Vergara, et al., "Implementation of a Reactive Dividing Wall Distillation Column in a Pilot Plant", vol. 25, pp. 229-234 (2008).

Smith, "Review of Glycol Ether and Glycol Ether Ester Solvents Used in the Coating Industry", Environ. Health Perspectives, vol. 57, pp. 1-4 (1984).

* cited by examiner

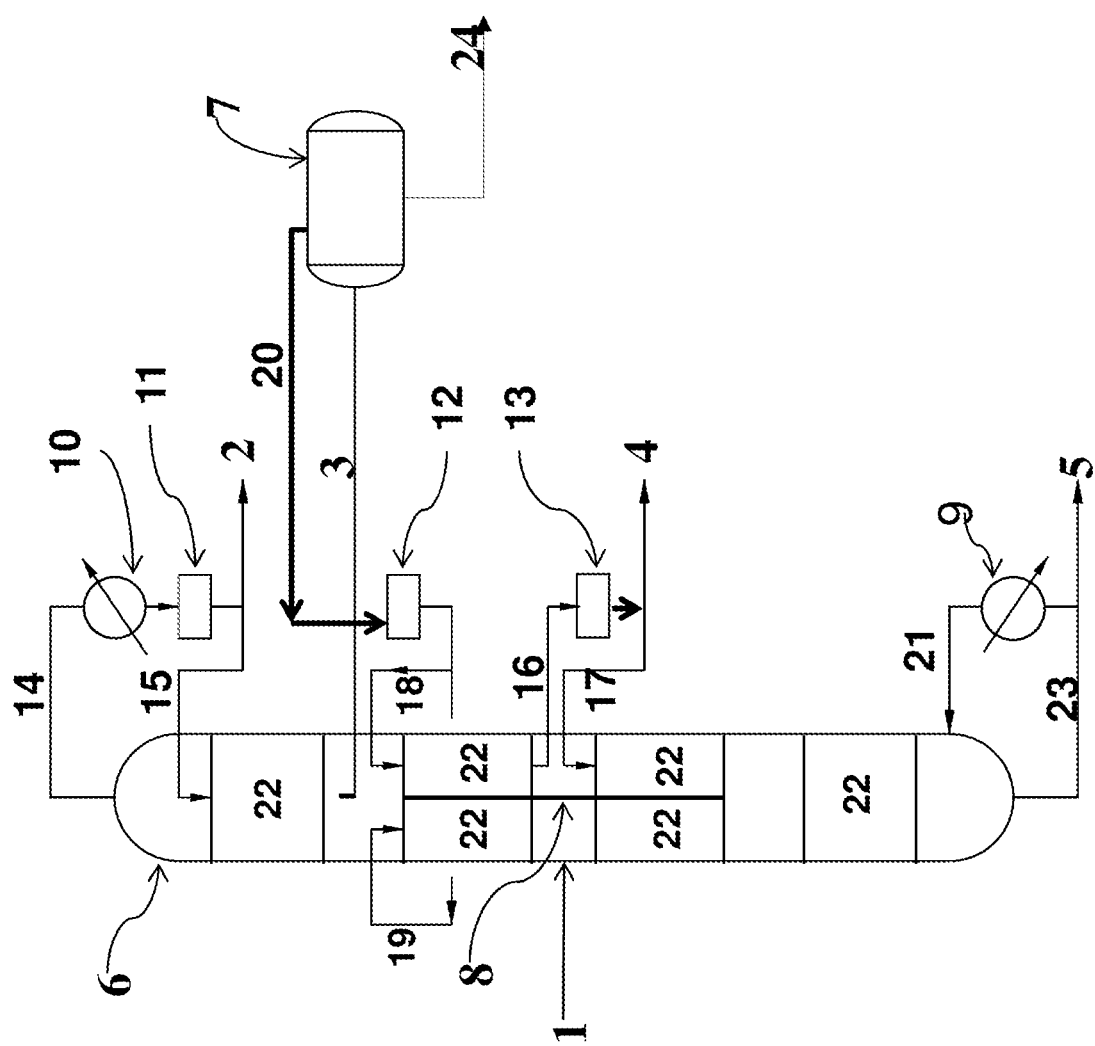

PROCESS FOR PURIFICATION OF METHYL METHACRYLATE

BACKGROUND OF THE INVENTION

The invention relates to a process for purification of a reaction product from preparation of methyl methacrylate, which also contains methanol, water and oligomers of methyl methacrylate.

Dividing wall columns are well known for their increased efficiency in separating three-component mixtures. In some cases dividing wall columns are combined with a water separator at the top of the column, see, e.g., Q.-K. Le et al., *Chemical Engineering Research and Design* (2015), http://dx.doi.org/10.1016/j.cherd.2015.03.022. There is a need for a more efficient process for separating the components of reaction products resulting from preparation of methyl methacrylate.

SUMMARY OF THE INVENTION

The present invention is directed to a process for purifying methyl methacrylate; said method comprising: (a) feeding a product mixture comprising methyl methacrylate, methanol, water and oligomers of methyl methacrylate to a distillation column comprising a dividing wall; (b) removing an overhead stream and a bottoms stream from the distillation column, and removing a middle side draw stream from the distillation column; wherein the crude product enters the dividing wall distillation column on an opposing side of the dividing wall from the middle side draw stream; and (c) removing an upper side draw stream from a point above the dividing wall and below the top of the distillation column, separating a portion of water from the upper side draw stream to produce a dewatered upper side draw stream and returning the dewatered upper side draw stream to the distillation column.

BRIEF DESCRIPTION OF THE DRAWING

The FIGURE is a schematic of a process of the invention using a dividing wall column.

DETAILED DESCRIPTION OF THE INVENTION

All percentage compositions are weight percentages (wt %), and all temperatures are in ° C., unless otherwise indicated. Oligomers of methyl methacrylate comprise the dimer of methyl methacrylate and smaller amounts of higher oligomers, including, e.g., the trimer. A "stage" is a tray in the case of a tray tower or an equilibrium stage in the case of a packed tower.

The dividing wall distillation column comprises a dividing wall. The dividing wall vertically bisects a portion of the interior of the distillation column creating a divided section but does not extend to the top or bottom sections of the column, thus enabling the column to be refluxed and reboiled in the same way as a conventional column. The dividing wall separates the column into two sides neither of which has a cross-sectional area exceeding 60% of the cross-sectional area of the column, preferably neither side exceeds 55%, preferably the sides are substantially equal, i.e., neither side exceeds 51%. The dividing wall provides a fluid impermeable baffle separating the interior of the column. The feed inlet to the column is located on one side of the dividing wall while one or more side draws are located on the opposing side. The dividing wall enables the side of the column that does not have the inlet to function in a more stable manner with minimal effect from fluctuations in inlet flow rates, conditions or composition. This increased stability enables the column to be designed and operated in a manner that allows one or more side draw streams having different compositions from either the overhead stream or the bottoms stream to be removed from the column. Preferably, the dividing wall does not extend vertically more than 70% of the total column height, preferably not more than 65%, preferably not more than 60%. Preferably, the dividing wall extends vertically at least 40% of the column height, preferably at least 45%, preferably at least 50%. Preferably, the vertical center of the dividing wall is at a distance from the bottom of the column which is 40 to 60% of the height of the column, preferably 45 to 55%. Preferably, the number of stages in the divided section is from 6 to 15, preferably from 8 to 13, preferably from 9 to 12.

Preferably the section of the column above the dividing wall has from 2 to 6 stages, preferably 3 to 5. Preferably the section of the column below the dividing wall has from 2 to 6 stages, preferably 3 to 5. Preferably, vapor from the section below the dividing wall is split between the divided sections such that no more than 60% of the vapor is passed to either side, preferably no more than 55%, preferably no more than 52%.

The temperature and pressure in the distillation column is dependent on the composition of the material being distilled. In one embodiment of the invention, the column is operated at reduced pressure, such as from about 1 to about 50 mmHg, or from 5 to 10 mmHg. The reboiler temperature advantageously is from 120 to 195° C.

The ability to make three or more product streams from a single column can enable component separation with fewer distillation columns and possibly reduced capital costs. The dividing wall distillation column can be used as a sole distillation column or multiple dividing wall distillation columns can be employed, either in series or parallel arrangements. The dividing wall distillation column can also be used in conjunction with one or more conventional distillation columns or separation devices. Embodiments of the invention can be particularly applicable when the optimum feed location to the column is above the optimum side draw location. If the feed location is above the side draw location in a conventional distillation column, the downward flow of the liquid feed within the column will have a significant effect on the side draw composition. Variations in the feed flow rate, conditions or composition of the feed stream will alter the side draw composition and make the production of a stable side draw stream very difficult to achieve in this configuration of a conventional distillation column.

Preferably, the feed enters the column at a distance from the bottom of the dividing wall which is 35 to 65% of the height of the dividing wall, preferably 40 to 60%, preferably 45 to 55%. Preferably, the middle side draw stream is removed from the column at a distance from the bottom of the dividing wall which is 35 to 65% of the height of the dividing wall, preferably 40 to 60%, preferably 45 to 55%. Preferably, a portion of the middle side draw stream is returned to the column, preferably from 70 to 90%, preferably at least 85%, preferably at least 87%; preferably no more than 90%, preferably no more than 95%.

Preferably, the upper side draw stream is removed from the column at a stage immediately above the divided section of the column Typically the upper side draw stream comprises two liquid phases. Preferably, the dewatered upper side draw stream is returned to the column at a height one stage lower than the one from which the upper side draw stream is removed. The dewatered upper side draw stream is split between the divided sections of the column, preferably such that no more than 60% of the stream is returned to either side, preferably no more than 55%, preferably no more than 52%. Preferably, the dewatered side stream contains only one liquid phase. Preferably, the dewatered side stream contains no more than 11 mole % water, preferably no more than 10%, preferably no more than 9.5%, preferably no more than 9%. Preferably, the volume of the upper side draw stream is at least 90% of the volume of liquid in the column stage from which it is removed, preferably at least 95%.

Water may be decanted from the stream by the means of standard methods. In one preferred embodiment, by means of a vessel that contains a vertical baffle or a series of baffles and is sized sufficiently that the organic and aqueous phase separate into individual phases. The lighter phase organic proceeds over the vertical baffle and the heavier water phase flows underneath the baffle. The separated liquids are withdrawn from the sections of the vessel that have accumulated the overflow and underflow of each phase.

The type of distillation column can be selected according to criteria well known to those skilled in the art. For example, a distillation column can include trays or packing, such as low pressure drop wire gauze structured packing.

The FIGURE depicts a dividing wall column 6 into which the feed 1 is introduced on one side of the column. The sections of the column marked 22 contain either packed beds or trays, while 8 is the dividing wall. Bottoms, 23 from the column are split, with bottoms product 5 removed from the column and recycle 21 returned to the column through reboiler 9. Liquid middle side draw stream 16 goes into splitter 13, with product stream 4 leaving the column and a reflux stream 17 returned to the column. Liquid upper side draw stream 3 leaves the column and enters water separator 7, with a water-rich liquid stream 24 leaving the column and a water-depleted liquid stream 20 is sent to a splitter 12 from which streams 18 and 19 are returned to the column. Distillate 14 leaves the column at the top and passes through condenser 10 and then splitter 11, with top draw 2 removed from the column and recycle stream 15 returned to the column.

EXAMPLES

Rigorous simulations were performed using ASPEN PLUS Version 8.6 software. The individual components that together rigorously represent the dividing wall tower are simulated using the module named RADFRAC within the Aspen suite. The decanter is simulated using the DECANTER module within the Aspen framework. Physical properties are modeled using an activity coefficient model for the liquid phase and an equation of state for the vapor phase.

Parameters used for simulation of the dividing wall column with a water separator were as follows: ten stages in the divided section of the column, with feed entering at the fifth stage; four stages above the divided section; four stages below the divided section; and the dividing wall in the middle. Heat is input in this example with a conventional reboiler located at the bottom of the tower.

Parameters used for simulating a dividing wall column without a water separator were the same as those used above except for the absence of the separator.

The two-column configuration has the bottoms from the first column fed to the second column, from which the product stream is collected overhead. Parameters used for simulation were as follows:

The first column, consisting of 10 stages, a condenser above the tower, and a reboiler, is fed at or near the top tray of the tower. The vapor from the overhead of the first tower proceeds to a condenser and a decanter after condensation. The organic phase of the decanter is fed back to the tower, while the aqueous phase proceeds out of the system for further processing. The bottom product from the first tower proceeds to the second tower, which was simulated with 8 stages. The tower is fed at or near the middle of the tower, with the overhead of the second tower being the finished product, this being the stream that corresponds to the middle product of the Dividing Wall Tower described in this document. The bottoms of the second tower contain the heavy oligimers, and may also contain traces of MMA product.

Example

The results for the claimed process are as follows:

|  | Feed | upper side draw | dewatered upper side draw[1] | middle side draw (product) | top draw | bottoms |
|---|---|---|---|---|---|---|
| Mole Flow kmol/hr | | | | | | |
| $H_2O$ | 15.76434 | 40.29813 | 16.13485 | 1.07E−05 | 7.735897 | 4.71E−11 |
| MEOH | 0.332871 | 0.202721 | 0.098506 | 5.92E−07 | 0.327164 | 2.64E−11 |
| MMA | 175.2585 | 336.3098 | 168.1406 | 171.8874 | 0.026643 | 3.315281 |
| MADIMER | 9.601292 | 9.93E−06 | 4.96E−06 | 0.112519 | 3.08E−13 | 9.488945 |
| Mole Frac | | | | | | |
| $H_2O$ | 0.078446 | 0.106939 | 0.087506 | 6.19E−08 | 0.956265 | 3.68E−12 |
| MEOH | 1.66E−03 | 5.38E−04 | 5.34E−04 | 3.44E−09 | 0.040442 | 2.06E−12 |
| MMA | 0.872119 | 0.892464 | 0.911899 | 0.999346 | 3.29E−03 | 0.258921 |
| MADIMER | 0.047778 | 2.63E−08 | 2.69E−08 | 6.54E−04 | 3.81E−14 | 0.741079 |
| Mass Flow kg/hr | | | | | | |

-continued

| | Feed | upper side draw | dewatered upper side draw[1] | middle side draw (product) | top draw | bottoms |
|---|---|---|---|---|---|---|
| $H_2O$ | 283.9994 | 725.9829 | 290.6741 | 1.92E−04 | 139.3645 | 8.48E−10 |
| MEOH | 10.66589 | 6.495617 | 3.156358 | 1.90E−05 | 10.48303 | 8.44E−10 |
| MMA | 17546.41 | 33670.44 | 16833.78 | 17208.91 | 2.667418 | 331.9171 |
| MADIMER | 1345.928 | 1.39E−03 | 6.95E−04 | 15.77319 | 4.32E−11 | 1330.179 |

[1]Amounts listed are for half of the dewatered upper side draw. The dewatered upper side draw is split equally between the two sides of the divided section With the same number of stages and the same duty to the reboiler the recovery of product is some 8 kilogram moles per hour higher of product of almost 5% higher purity as obtained from a dividing wall column without a water separator (see Comparative Example 1).

With the same number of stages and the same duty to the reboiler the recovery of product is some 12.2 kilogram moles per hour higher of product at essentially the same purity as in the two-column configuration (see Comparative Example 2). This amounts to 1222 kilograms per hour (roughly 10.5 MM kilograms per year at 8600 hours per year) for no additional duty and no additional stages, with one less tower shell and foundation.

Comparative Example 1

The results for use of a dividing wall column without a water separator are as follows:

| | Feed | middle side draw (product) | top draw | bottoms |
|---|---|---|---|---|
| Mole Flow kmol/hr | | | | |
| $H_2O$ | 15.76434 | 8.033197 | 7.731109 | 4.71E−11 |
| MEOH | 0.3328706 | 0.000172014 | 0.3326982 | 2.64E−11 |
| MMA | 175.2585 | 163.9426 | 0.0268486 | 3.315281 |
| MADIMER | 9.601292 | 0.0239966 | 0 | 9.488945 |
| Mole Frac | | | | |
| $H_2O$ | 0.0784463 | 0.0467046 | 0.9555602 | 3.68E−12 |
| MEOH | 0.00165643 | 1.00E−06 | 0.0411212 | 2.06E−12 |
| MMA | 0.8721193 | 0.9531547 | 0.00331848 | 0.258921 |
| MADIMER | 0.0477778 | 0.000139516 | 0 | 0.741079 |
| Mass Flow kg/hr | | | | |
| $H_2O$ | 283.9994 | 1.92E−04 | 139.2782 | 0.000649077 |
| MEOH | 10.66589 | 0.00551169 | 10.660370 | 2.90E−07 |
| MMA | 17546.41 | 16413.49 | 2.6880180 | 1130.229 |
| MADIMER | 1345.928 | 3.3639 | 0 | 1342.564 |

Comparative Example 2

The results for use of two columns are as follows:

| | overhead from column 1 | product (top of column 2) | bottoms from column 2 |
|---|---|---|---|
| Mole Flow kmol/hr | | | |
| $H_2O$ | 16.54821 | 7.66E−08 | 8.76E−16 |
| MEOH | 0.1929004 | 8.09E−08 | 7.87E−15 |
| MMA | 16.47888 | 159.6864 | 1.268949 |

-continued

| | overhead from column 1 | product (top of column 2) | bottoms from column 2 |
|---|---|---|---|
| MADIMER Mole Frac | 0.1095942 | 0.0228142 | 8.117651 |
| $H_2O$ | 0.4964363 | 4.80E−10 | 9.30E−17 |
| MEOH | 0.0057869 | 5.07E−10 | 8.35E−16 |
| MMA | 0.4943563 | 0.999854 | 0.1347327 |
| MADIMER | 0.00328776 | 0.000142848 | 0.8619047 |

The invention claimed is:

1. A process for purifying methyl methacrylate; said method comprising: (a) feeding a product mixture comprising methyl methacrylate, methanol, water and oligomers of methyl methacrylate to a divided section of a distillation column comprising a dividing wall; (b) removing an overhead stream and a bottoms stream from the distillation column, and removing a middle side draw stream from the distillation column; wherein the crude product enters the dividing wall distillation column in a divided section on an opposing side of the dividing wall from the middle side draw stream; and (c) removing an upper side draw stream from a point above the dividing wall and below the top of the distillation column, separating a portion of water from the upper side draw stream to produce a dewatered upper side draw stream and returning the dewatered upper side draw stream to the distillation column.

2. The process of claim 1 wherein the dividing wall has a height from 45 to 65% of total column height.

3. The process of claim 2 wherein the dividing wall separates the column into two sides neither of which has a cross-sectional area exceeding 60% of cross-sectional area of the column.

4. The process of claim 3 wherein a vertical center of the dividing wall is a distance from a bottom of the column which is 40 to 60% of a height of the column.

5. The process of claim 4 wherein the dewatered upper side draw stream contains no more than 10 mole % water.

6. The process of claim 5 wherein volume of the upper side draw stream is at least 90% of the volume of liquid in the column stage from which it is removed.

7. The process of claim 6 in which the crude product enters the column at a distance from a bottom of the column which is 40 to 60% of a height of the column.

8. The process of claim 7 in which the upper side draw stream is removed from the column at a stage immediately above the divided section of the column.

9. The process of claim 8 in which the dewatered upper side draw stream is returned to the column at a height one stage lower than the top of the divided section.

10. The process of claim 9 in which the dewatered upper side draw stream contains no more than 9 mole % water.

* * * * *